United States Patent [19]

Spencer et al.

[11] Patent Number: 5,209,800
[45] Date of Patent: May 11, 1993

[54] TOTAL CONTAINMENT WELDING OF PLASTIC TUBES

[75] Inventors: Dudley W. C. Spencer; John B. Shaposka; Robert J. Beird, all of Wilmington, Del.

[73] Assignee: Denco, Inc., Wilmington, Del.

[21] Appl. No.: 764,249

[22] Filed: Sep. 23, 1991

Related U.S. Application Data

[63] Continuation-in-part of Ser. No. 682,977, Apr. 10, 1991, which is a continuation-in-part of Ser. No. 604,979, Oct. 29, 1990, which is a continuation-in-part of Ser. No. 569,855, Aug. 20, 1990.

[51] Int. Cl.⁵ .................. B29C 57/10; B29C 65/20
[52] U.S. Cl. ..................................... 156/158; 156/251; 156/258; 156/304.2; 156/304.5; 156/304.6; 156/515; 156/518; 156/530
[58] Field of Search ............... 156/158, 304.2, 304.5, 156/304.6, 251, 258, 515, 518, 530

[56] References Cited

U.S. PATENT DOCUMENTS

| | | | |
|---|---|---|---|
| 3,968,195 | 7/1976 | Bishop | 264/154 |
| 4,737,214 | 4/1988 | Leurink et al. | 156/304.2 |
| 4,793,880 | 12/1988 | Shaposka et al. | 156/304.2 |
| 4,897,138 | 1/1990 | Shaposka et al. | 156/304.2 |

Primary Examiner—Caleb Weston
Attorney, Agent, or Firm—Connolly & Hutz

[57] ABSTRACT

A plastic tube is cut into two sections which are sealed closed by a sterile method wherein the tube is loaded into two clamping jaws which flatten the tube. The tube is cut through the flattened section and the cut ends are heated to their molten state. A wafer having wings is located between the cut ends with the wings penetrating the lumens to create an internal plug as the wings force the molten material inwardly. The plugs add to the strength of the resultant seal. If desired, the molten ends are pressed into a cavity which is cooled to a temperature below the molten temperature to seal the ends. The tubes are then removed from the cavity. When it is desired to connect individual tube sections the two tube sections are placed in clamp members in axial alignment slightly spaced from each other. The ends of the tube sections are melted by a melt/wipe process and the tube sections are then pressed into contact with each other to be welded into an integral tube. The same device is used for both the sterile disconnect and connect procedures.

34 Claims, 3 Drawing Sheets

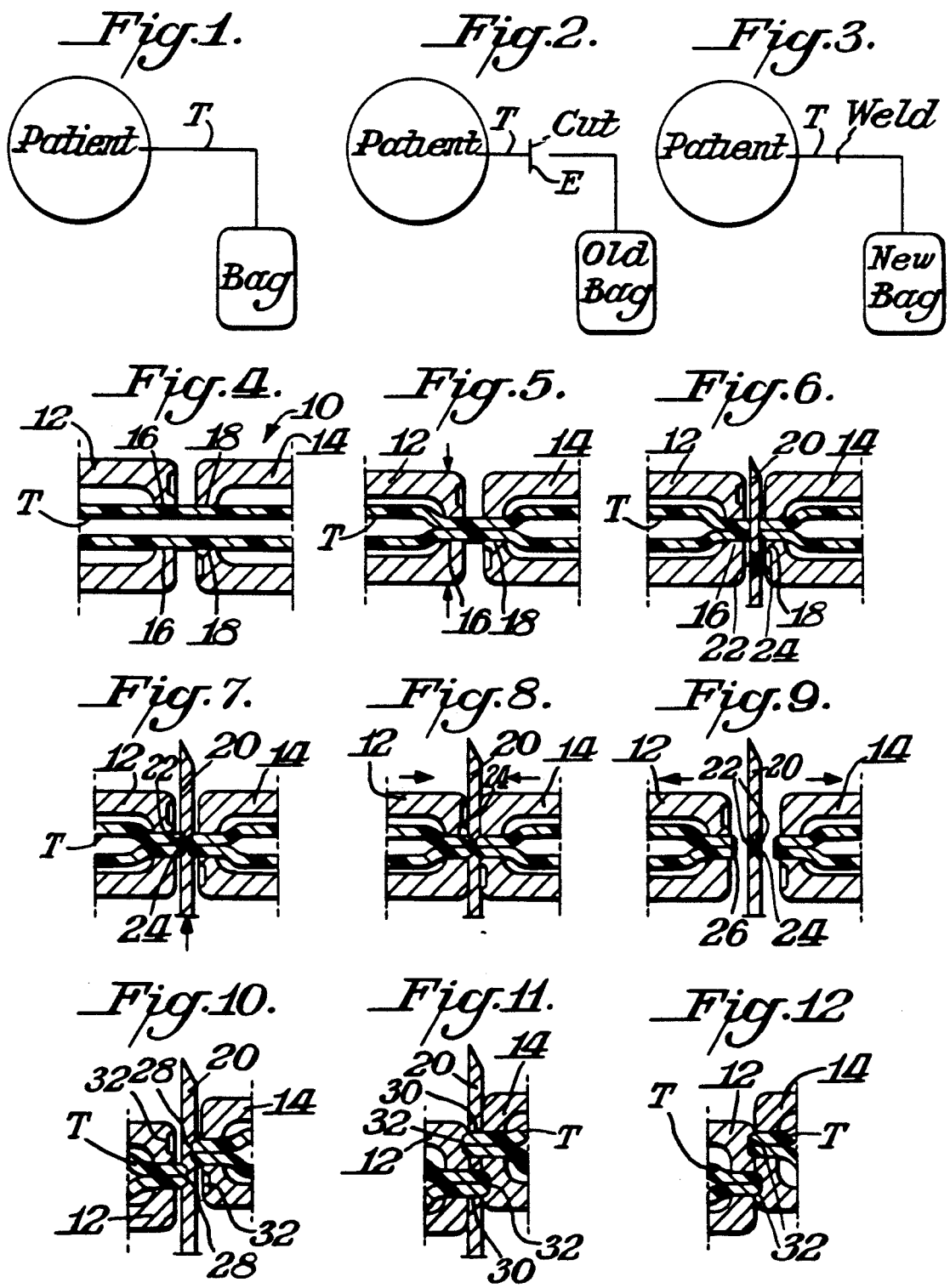

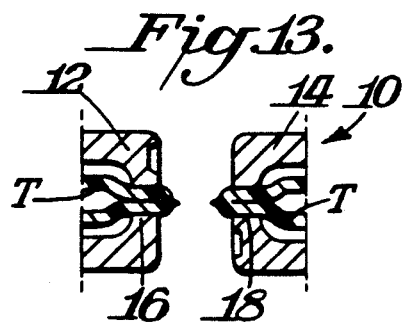
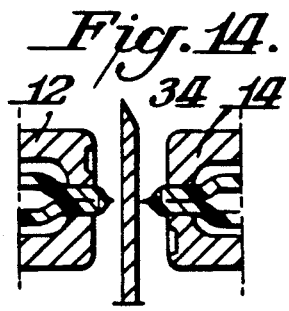
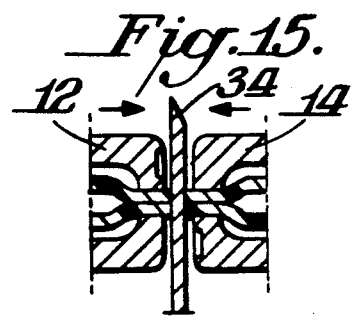
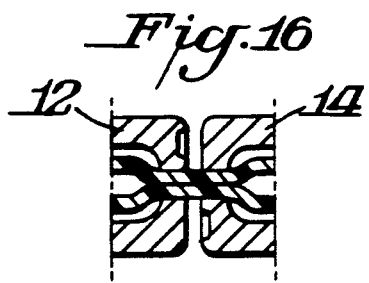
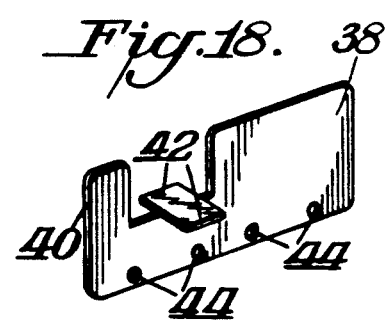
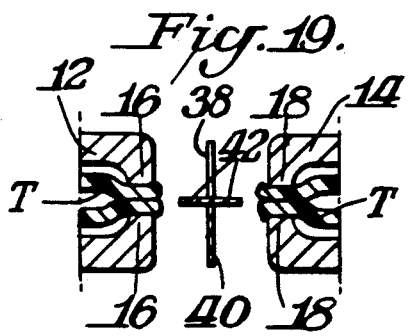
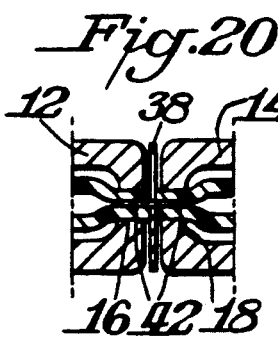
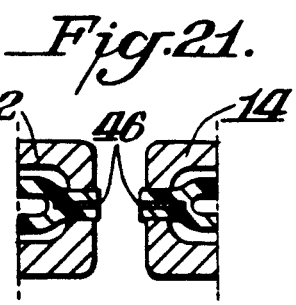
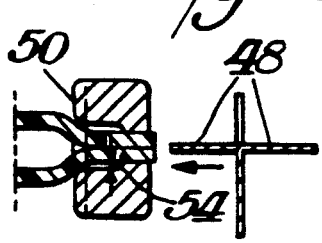
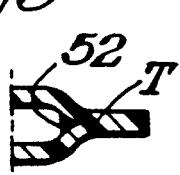

TOTAL CONTAINMENT WELDING OF PLASTIC TUBES

CROSS-REFERENCE TO RELATED APPLICATION

This application is a continuation-in-part of application Ser. No. 07/682,977 filed Apr. 10, 1991, which in turn is a continuation-in-part of Ser. No. 07/604,979 filed Oct. 29, 1990, which in turn is a continuation-in-part of Ser. No. 07/569,855 filed Aug. 20, 1990.

BACKGROUND OF INVENTION

The above noted parent applications, the details of which are incorporated herein by reference thereto, deal with various techniques for the total containment welding of plastic tubes where no contaminants can enter or leave the tube lumen. In general, the welding techniques involve an axially aligned, melt/wipe process where the ends of two tube sections are melted to be rendered into a molten state and then pressed together to become integral.

The above techniques are particularly desirable for widespread uses including CAPD, blood processing and other techniques where it is necessary to replace used consumables. In such practices, it is necessary to cut the tube leading from the used bag to the patient and then weld a new tube section from a fresh bag to the tube section leading from the patient. It would be desirable if the tube cutting or disconnect procedure and the tube joining or connect procedure could be made as simple as possible in order to avoid difficulties in performing these procedures.

SUMMARY OF INVENTION

An object of this invention is to provide a sterile tube disconnect technique which meets the above needs.

A further object of this invention is to provide a sterile tube connect technique which also meets the above needs.

In accordance with this invention, a tube is cut in a disconnect technique which involves loading the tube into two clamp jaws which flatten the tube. The flattened section is then cut to produce two cut ends which are heated to their molten state. The molten ends of the tubes are then inserted into close fitting cavities at a temperature below the molten state temperature for sealing the ends.

The cavities or depressions may be formed in the wafer itself which is used for cutting the tubes. The cavities may either be aligned with each other or may be offset from each other. Alternatively, the cavities may be formed in the clamped members and access would be had by means of holes or openings through the wafer.

In a preferred practice of the invention, the wafer includes a pair of flat projections in the form of wings which could be inserted into the flat lumen of each tube end to heat the lumen and further facilitate the sealing operation.

In the connect procedure the two individual tubes or tube sections are mounted in clamp members in axial alignment with each other and flattened by the clamp members. The flattened tube ends are then melted by a sterile melt/wipe procedure after which the melted tube ends are pressed into contact with each other to effect a welding. If desired, the welded section may be rolled to facilitate a reopening of the lumen. Advantageous the same device may be used for both the disconnect and connect procedures.

THE DRAWINGS

FIG. 1 is a schematic view illustrating a plastic tube being used to connect a bag, such as used in kidney dialysis to a patient;

FIG. 2 is a view similar to FIG. 1 wherein the tube is cut to permit removal of the used bag;

FIG. 3 is a view similar to FIGS. 1–2 illustrating the sequence in operation wherein a fresh or new bag is welded to the remaining tube sections;

FIG. 4 is a cross-sectional view of a total containment device used for the disconnect or tube cutting process, such as illustrated in FIG. 2 in the first stage of operation;

FIGS. 5–12 are views similar to FIG. 4 showing the sequential steps in the disconnect procedure;

FIG. 13 is a view similar to FIG. 4 showing the initial stage of the connect or welding procedure illustrated in FIG. 3;

FIGS. 14–16 are views similar to FIG. 13 showing the sequential steps in the connect procedure;

FIG. 17 is a cross-sectional view showing the welded portion of the tube section resulting from the connect procedure of FIGS. 13–16;

FIG. 18 is a perspective view of a wafer suitable for use in a disconnect procedure in accordance with this invention;

FIGS. 19–21 are views similar to FIG. 4 illustrating the sequence of steps in the disconnect procedure using the wafer of FIG. 18;

FIG. 22 is a view similar to FIG. 19 showing a disc connect procedure with a modified wafer;

FIG. 23 is a view similar to FIG. 22 showing the final sealed tube section; and

DETAILED DESCRIPTION

Figure 24:
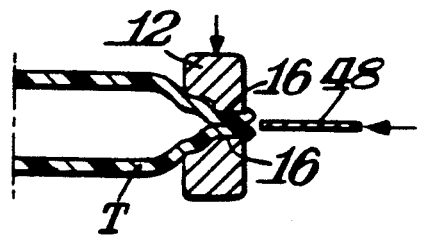
FIGS. 24–29 illustrate the sequence in the use of the wafer of FIG. 22.

It is to be understood that the present invention may be used whenever it is desirable to sterilely cut or to sterilely weld plastic tube sections for any purpose, such as indicated in the parent applications, the details of which are incorporated herein by reference thereto. The present description, however, will be directed to the use of the invention for the removal (disconnect) of an old or used consumable and a replacement (connect) of a new or fresh consumable.

FIG. 1 schematically illustrates a plastic tube made from any suitable plastic material, such as PVC wherein the tube T is used to provide a dialysate from the bag to the patient.

FIG. 2 illustrates how the tube T would be cut when it is necessary to replace the used or old bag. The sealed end E results which remains sealed until the new bag is welded thereto. Preferably, the free end of the tube leading to the old bag is also sealed, although such sealing is not absolutely necessary.

FIG. 3 illustrates the next sequence in operation wherein a plastic tube section leading from a new bag is welded to the sealed end E resulting from the cut in FIG. 2.

FIGS. 4–12 illustrate the practice of this invention as used for the disconnect procedure of FIG. 2. As shown therein, a disconnect device 10 includes a pair of clamp members 12,14 each of which has a pair of clamped jaws 16,18. A tube T is inserted between the two clamp members while the jaws 16,18 are in their unclamped condition. The single tube illustrated is of open and round configuration with fluid flowing through the lumen. The invention, however, may be practiced with tubes of other construction.

FIG. 5 illustrates the next sequence in operation wherein the clamp members 12,14 are actuated to move their jaws 16,18 into the clamping condition and thereby flatten the section of tube T as shown therein.

FIG. 6 illustrates the next step in the sequence of operation wherein a cutting member, preferably a hot wafer 20 is moved through the gap between the clamp members 12,14 to cut through the flattened section of tube T in that gap.

FIG. 7 illustrates the wafer 20 to move in the Y direction with the tubes being aligned in the X direction. It is to be understood, however, that the wafer may also move in the Z direction instead of the Y direction. What is necessary, is that the wafer move through the gap between the slightly spaced clamp members 12,14.

The hot wafer 20, not only cuts the tube T into two tube sections, but also the wafer would pause to heat the tube ends to a molten state.

After the tube ends become molten the wafer or heating means advances one tube increment presenting a dimpled area having a pair of aligned cavities or depressions 22,22 separated by a web 24 which more clearly shown in FIG. 9.

FIG. 7 illustrates the wafer or heating device 20 to be positioned so that the clamped cut tube ends are aligned with the depressions 22,22.

In the next sequence of operation illustrated in FIG. 8 the clamp members 12,14 are moved relatively toward each other so that each molten end of the cut tube is inserted into a corresponding depression in the wafer 20. Depressions 22,22 are dimensioned to snugly receive the tube ends. When in this position, the clamp members 12,14 also make surface contact with wafer 20. The result of this arrangement shown in FIG. 8 is to force the hot tube ends into the hot depressions 22 thus forming a tube end that is greater than or equal to the tube wall thickness. The cold clamp members, by contacting the wafer in the meantime, cool the wafer to thereby cool the molten tube ends and the wafer to ambient temperature.

When the clamp members 12,14 are withdrawn as illustrated in FIG. 9, the now cool wafer may be withdrawn and the separated cool tubes may be removed from the clamp members when the clamping jaws are moved to their unclamped condition. As shown in FIG. 9, the molten material 26 is left at the ends of the cut tube sections. The resultant seal would be able to withstand greater than 100 psi internal pressure.

The invention may be practiced with any suitable materials and any suitable dimensions. For example, the wafer 20 may have a thickness of 0.5 mm with the web 24 being 0.1 mm thick and each depression 22,22 being 0.2 mm deep. The wafer may be made of a copper blade having a teflon coating. The function of the depressions 22 is to confine the molten ends over a larger area than would result if the cut end simply contacted a flat surface. As a result, the sealed end is of somewhat bulbus form. In the preferred practice of the invention the wafer is heated to 280° C. to effect a melting operation and then is lowered to room temperature upon physical contact with the clamping members.

Although in the illustrated embodiment an open tube is being cut after being in a flattened condition, the invention could be practiced with preflattened tubes.

FIG. 10 illustrates a variation of the invention wherein the wafer 20 has offset cavities or depressions 28,28 for receiving the molten ends of the cut tubes. In this practice of the invention it would be necessary to axially displace the cut ends from each other by relatively moving the clamping members 12,14 out of alignment. The advantage of this arrangement is that the same size wafer could be used with deeper cavities. Alternatively the same size cavities could be used in a thinner wafer.

FIG. 11 illustrates yet another practice of the invention wherein the wafer 20 would have a pair of holes or openings 30,30 extending completely therethrough which can be aligned with corresponding cavities or depressions 32,32 in the clamping members 12,14. Thus, when the clamp members 12,14 are moved toward each other the molten ends would completely pass through the respective openings 30,30 in the wafer and penetrate into the corresponding depressions 32,32 of the clamping members to effect the cooling.

FIG. 12 illustrates yet another variation wherein during the cooling operation the wafer is completely removed and the cut ends extend directly into the cavities 32,32 of the clamp members 12,14.

FIGS. 13–17 relate to the welding operation, such as schematically illustrated in FIG. 3. In this arrangement, the same device 10 could be used which includes the pair of clamping members 12,14 having clamping jaws 16,18. As shown in FIG. 13 two single tubes after loading into the two clamp members 12,14 with the jaws 16,18 moved to their clamping condition are brought into axial alignment with one another. A hot cutting means, such as a wafer 34 at a temperature of, for example 260°–350° C. is placed between the tube ends, but not touching either tube as shown in FIG. 14.

In the next step of operation, both tubes are then axially advanced into contact with the cutting member 34 to accomplish the melt phase of the melt/wipe action. FIG. 15 illustrates by the arrows, the movement of the clamp members 12,14 toward each other.

After the melt phase is completed the heater 34 is completely withdrawn as shown in FIG. 16 taking the excess plastic with it and forming two hot tube faces that can be urged together to form a weld.

The welded tube can then be rolled to reopen the lumen as illustrated in FIG. 17 which also illustrates the weld 36. Rolling could be accomplished in the manner similar to twisting a pencil in the finger tip. The gentle rolling action breaks the internal seal thus reestablishing the lumen. Alternatively, the tube can be opened by a gentle compression.

As previously discussed, FIGS. 4–9 illustrate a practice of the invention wherein the cut tube ends remain aligned with each other. FIGS. 10–12 illustrate three alternatives which involve offsetting the tube ends during the quenching operation. The advantage of the axial arrangement is the simplicity in avoiding the need for the offsetting step. There are advantages to the offsetting arrangement. For example, in the variation of FIG. 10, either a thinner wafer could be used with cavities of the same size as in FIG. 9 or the same thickness wafer could be used with deeper cavities. FIGS. 11–12 have the advantage of using the clamp member itself to provide the quenching step. In its broadest aspect the invention may be practiced by having the depressions in members other than the wafer or clamp members. These other members would be located near the clamp members.

FIGS. 18-21 illustrate a further variation of the invention used in the disconnect procedure. FIG. 18 illustrates an improved wafer or heating device 38 which has a lead section 40 which would function to accomplish the cutting action. If desired the lead section may be tapered to have a pointed lead edge. A pair of projections in the form of wings 42 extend perpendicularly from each side of the main wafer body 48. A series of alignment holes 44 are provided along one edge of wafer 38. Alignment holes 44 would be viewed by a sensor in the wafer holder to assure proper positioning of the wafer in the holder.

In this practice of the invention a single tube of, for example, open and round configuration would be loaded into two clamp members 12,14 in the manner illustrated in FIG. 4. Clamp jaws 16,18 would be moved to their closed position squashing the tube into a flat configuration as illustrated in FIG. 5. Heating means such as the wafer 38 which would be heated to, for example, 180°-350° C. is passed through the tube with the lead end 40 separating the tube into two ends. The separated tube ends are then moved away from each other and away from lead end 40 and the wafer 38 is advanced one tube increment to the position shown in FIG. 19 wherein the two wings 42,42 are aligned at the tube face. The clamp members 12,14 are then moved toward each other driving the protrusions or wings 42,42 into the tube lumen a distance of for example 3 mm. Wings 42 may be are flat, tapered or contoured and dimensioned to snugly fit into the flat lumens to heat the lumens. As shown in FIG. 20 the clamp members 12,14 are again withdrawn removing the wings 42,42 from the tube lumen. The built in elastic memory of the plastic is then allowed to assist in sealing the molten interface 46 as shown in FIG. 21. The clamp jaws may be spring loaded to assure full bonding. The tube ends could then be allowed to cool using the heat transfer (heat sink) reservoir of the clamp members to quench or cool the seal rapidly in the manner previously illustrated such as with the embodiment of FIG. 12. The resultant seal is sufficiently strong to withstand a bursting of the tubing wall without seal failure.

FIGS. 22-29 illustrate a variation of the invention described in FIGS. 18-21. The embodiment of FIGS. 22-29 represents a significant advancement in the art. In the embodiment of FIGS. 18-21 the wings 42,42 extend a distance which terminates below the contact surfaces of clamping jaws 16,18 as shown in FIG. 20. In the embodiment of FIG. 22, however, the wings 48 extend beyond the contact surface of the clamping jaws. Further extension of the wings 48 is based upon the recognition that when a wing is pushed into the clamp the section between the clamping surfaces is melted which causes it to become thinned. An improved seal can be obtained where there is also a melting inwardly of the clamping surfaces to the area indicated by the dotted line 50. The result of this extension of the wings is to deposit a small amount of plastic material, such as PVC at the tube wall junction. This deposit of material or plug is indicated by the reference numeral 52 in FIG. 23. This arrangement increases the strength of the tube and is a key factor in providing a particularly strong seal.

Figure 25:
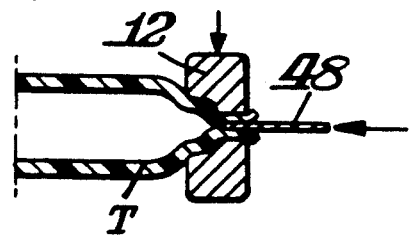
Figure 26:
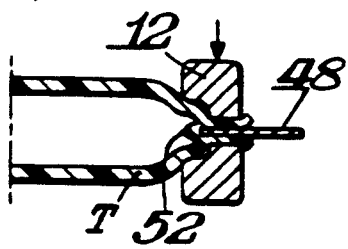
Figure 27:
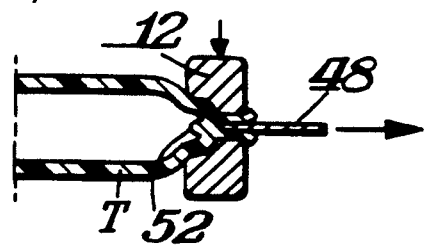
Figure 28:
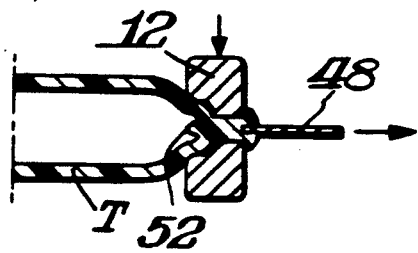
Figure 29:
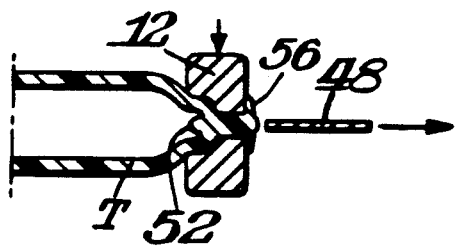

FIGS. 24-29 illustrate in greater detail the sequence of operation for the embodiment of the invention shown in FIGS. 22-23. For the sake of simplicity FIGS. 24-29 show only one of the clamp members, namely, clamp member 12 with its clamp jaws 16 and one of the tube ends T as well as one of the wings 48. As shown in FIG. 24 one of the clamp jaws, such as the upper clamp jaw is moveable to flatten the end of tube T and permit the flattened section to be cut so that the wing 48 may enter the flat lumen. When the wing enters the lumen, it pushes the molten material, such as PVC in front of it as shown in FIG. 25. Because of pressure on this area the only direction the PVC can go is inwardly. FIG. 26 illustrates the condition where wing 48 has been inserted its maximum penetration with the displaced PVC forming a plug 52. Wing 48 pauses to heat the tube. FIG. 27 illustrates wing 48 as it is being removed from the flat lumen. As shown therein, the molten material in the flat lumen creates a seal area. The excess material still remains as a plug 52. FIG. 28 shows wing 48 as it is about to be completely removed from the flat lumen which is at this time is sealed. FIG. 29 shows the condition of tube T when wing 48 has been completely removed. As clearly shown therein, a seal is formed along the length of the flat lumen as well as inwardly at plug 52. Plug 52 adds to the strength of the resultant seal. Tests indicate that the main strength of the seal, in fact, comes from the area around the plug rather than the area between clamp jaws 16. As shown in FIG. 29 a secondary plug 56 is formed when wing 48 is removed from the flattened lumen.

The arrangement of FIGS. 22-29 also avoids another problem which occurs where the wings do not penetrate beyond the contact surfaces of the clamping jaws. This problem is the wall thinning on the inboard clamp side caused by the tube tending to be round. Adding a 20 mil. step 54 to the clamp jaws restrains the tube rounding tendency thereby eliminating this problem. Step 54 is dimensioned to provide enough space to provide relief but is sufficiently close to the flattened tube to resist its tendency to return to its round position. Preferably the step height is 10% of the tubing outside diameter.

The embodiment of FIGS. 22-29 also addresses the problem of potential vertical misalignment of the seal. Such misalignment might be caused from starting the wing at the center and having weight on only one side. Since the tube melts, the center line changes. Accordingly, if the start where at the center, by the end of the melting it is no longer the center. The center line of the finished seal can be predetermined by using balanced or unbalanced clamp forces. For example, in a sterile connection instrument where clamping forces are generated by a lid closure against a stationary bed, a clamping force (and tube melting follow-up) are unbalanced. To maintain the melt closure center line therefore, the wing should enter the assembly slightly off center to the assembly to compensate for the force of follow up imbalance.

It is to be understood that various aspects of the invention may be used in combination with or separately from each. Thus, for example, the wing penetration techniques may be used with or without the quenching techniques. Preferably, the same device is used in both the disconnect and connect techniques. If desired separate devices may be used for each technique. Where the same device is used for both connect and disconnect, the melt/wipe would be done on a flat portion of the wafer in line with but displaced from the wings.

The invention may be used in a wide range of applications including Blood Processing, CAPD—Renal, Plasma pherisis, Fractionation, Urinary drainage, Biotech, Hospital Pharmacea, General Bio & Chem lab usage, Chemo-therapy, TPN, and IV solution additions.

Similarly, the consumables that may be disconnected/connected include Filters, Membranes, Assays, Nutrients, Innoculants, Buffers, Antibiotics, Isotopes, Hepatitis & AIDS indicators, and Samples.

As can be appreciated the invention provides sterile techniques which may be practiced in a simplified manner without sacrifice to reliability in the cutting or welding of tube sections.

What is claimed is:

1. A sterile disconnect method for cutting a plastic tube and producing two sealed ends comprising placing the plastic tube in a pair of spaced clamp members, closing the clamp members to flatten a section of the tube, cutting through the flattened tube section to create a pair of tube ends, heating the tube ends to their molten state, inserting each tube end in a snug fitting depression, quenching each tube end by its depression being at a temperature below the molten state temperature of the tube end, removing each tube end from its depression with the tube end being sealed, and the depressions being in the tool for heating the tube ends.

2. The method of claim 1 wherein the tube section is completely flattened to close any lumen therein.

3. The method of claim 1 wherein the cutting and heating steps are done by the same tool.

4. The method of claim 1 wherein the depressions are offset from each other, and the clamp members are shifted with respect to each other to align each tube end with its respective depression.

5. The method of claim 1 wherein the clamp members contact the tool during the quenching step to lower the temperature of the tool.

6. The method of claim 1 wherein the depressions are aligned cavities separated by a web.

7. The method of claim 1 wherein the depressions are formed in the clamp members.

8. The method of claim 7 wherein the tool is removed from between the clamp members before the tube ends are inserted into the depressions.

9. The method of claim 7 wherein the tool has two holes therethrough alignable with the depressions, and each tube end is inserted through a respective hole and into its depression.

10. A sterile disconnect method for cutting a plastic tube and producing two sealed ends comprising placing the plastic tube in a pair of spaced clamp members, closing the clamp members to flatten a section of the tube, cutting through the flattened tube section to create a pair of tube ends, heating the tube ends to their molten state, inserting each tube end in a snug fitting depression, quenching each tube end by its depression being at a temperature below the molten state temperature of the tube end, removing each tube end from its depression with the tube end being sealed, the heating being done by a wafer having a flat surface perpendicular to the tube ends and a pair of oppositely extending wings, contacting the exposed faces of the tube ends against the flat surface, and penetrating the wings into the lumens of the tube ends to melt the exposed faces and the wing contacting surfaces of the lumens.

11. The method of claim 10 wherein the clamp members have jaws with tube contacting surfaces, and penetrating the wings in the lumen beyond the tube contacting surfaces.

12. The method of claim 11 including forming a plug inwardly of the flattened lumen of each tube end to form a seal.

13. The method of claim 11 including providing a step on each clamp member jaw inwardly of its contacting surfaces, and spacing the tube from the step by a distance of about 10% of the tube outside diameter to permit some relief by each step while resisting the tendency of the tube to return to its unflattened condition.

14. A sterile disconnect method for cutting a plastic tube and producing two sealed ends comprising placing the plastic tube in a pair of spaced clamp members, closing the clamp members to flatten a section of the tube, cutting through the flattened tube section to create a pair of tube ends, inserting a heated wafer between the tube ends with the wafer having a flat surface perpendicular to the tube ends and having a pair of oppositely extending wings, contacting the exposed faces of the tube ends against the flat surface, penetrating the wings into the lumens of the tube ends to melt the exposed faces the wing contacting surfaces of the lumens, removing the wafer from contacting the tube ends, and forming a sterile seal in each tube end from its melted surfaces.

15. The method of claim 14 including using the same device which disconnects to form the tube ends to connect one of the tube ends to a further tube end.

16. The method of claim 14 wherein the clamp members have jaws with tube contacting surfaces, and penetrating the wings in the lumen beyond the tube contacting surfaces.

17. The method of claim 16 including forming a plug inwardly of the flattened lumen of each tube end to form a sterile seal.

18. The method of claim 16 including providing a step on each clamp member jaw inwardly of its contacting surfaces, and spacing the tube from the step by a distance of about 10% of the tube outside diameter to permit some relief by each step while resistant the tendency of the tube to return to its unflattened condition.

19. A method of forming a sterile welded joint form two plastic tube ends which are initially closed including the steps of mounting the tubes in their straight unbent condition in two axially aligned clamp members with the tube ends extending beyond the clamp members and toward each other, relatively moving a heater between the spaced tube ends, contacting the tube ends against the heater in a melt/wipe operation wherein the heater wipes against the unbent tube ends to melt the tube ends and the tube ends are welded together when the heater is removed and the tube ends are pressed into contact against each other, and re-opening the tube ends to form a continuous lumen.

20. The method of claim 19 wherein the heater is moved between the spaced tube ends.

21. The method of claim 19 including closing clamp jaws against each tube end to flatten the tube end before the melt/wipe operation.

22. The method of claim 19 wherein the tube ends are opened by a pressure/rolling action.

23. A device for the cutting of a plastic tube and the sterile sealing of the resulting tube ends comprising a pair of aligned clamp members having clamping jaws for flattening a tube section of a tube inserted into and across said clamp members, a cutting member movable into the space between said clamp members for cutting through the flattened tube section to create a pair of tube ends, a heated wafer for contacting and melting the exposed faces of the tube ends, a pair of exposed quenching depressions into which the heated tube ends may be inserted to lower the temperature of the heated tube ends to seal the tube ends, said depressions being formed in said wafer, and said clamp members being movable into contact with said wafer to lower the temperature of said wafer.

24. The device of claim 23 wherein said depressions are aligned cavities separated by a web.

25. The device of claim 23 wherein said heater wafer is also said cutting member.

26. The device of claim 23 wherein said depressions are offset from each other.

27. In a heated wafer for cutting through a flattened tube section to create a pair of tube ends, the improvement being in that said wafer has a main body portion which is plate like to form a flat surface for being disposed against each exposed face of the tube ends, and a pair of oppositely extending wings perpendicular to said body portion for penetrating into the flat lumens of the tube ends.

28. The wafer of claim 27 wherein said body portion has a lead end which comprises cutting means for cutting through the tube section.

29. A method of forming a sterile welded joint from two plastic tube ends which are initially closed including the steps of mounting the tubes in their straight unbent condition in two axially aligned clamp members with the tube ends extending beyond the clamp members and toward each other, disposing a heater between the spaced tube ends, contacting the tube ends against the heater so that the heat from the heater melts the tube ends, removing the heater from between the melted tube ends, pressing the melted tube ends into contact with each other to weld the tube ends together and form a single tube, and re-opening the tube ends to form a continuous lumen.

30. A device for the cutting of a plastic tube and the sterile sealing of the resulting tube ends comprising a pair of aligned clamp members having clamping jaws for flattening a tube section of a tube inserted into and across said clamp members, a cutting member movable into the space between said clamp members for cutting through the flattened tube section to create a pair of tube ends, a heated wafer for contacting and melting the exposed faces of the tube ends, a pair of exposed quenching depressions into which the heated tube ends may be inserted to lower the temperature of the heated tube ends to seal the tube ends, said depressions being formed in said wafer, and said clamp members being movable into contact with said wafer to lower the temperature of said wafer.

30. A device for the cutting of a plastic tube and the sterile sealing of the resulting tube ends comprising a pair of aligned clamp members having clamping jaws for flattening a tube section of a tube inserted into and across said clamp members, a cutting member movable into the space between said clamp members for cutting through the flattened tube section to create a pair of tube ends, a heated wafer for contacting and melting the exposed faces of the tube ends, a pair of exposed quenching depressions into which the heated tube ends may be inserted to lower the temperature of the heated tube ends to seal the tube ends said depressions being formed in said clamp members, and said wafer having a pair of holes extending therethrough and alignable with said depressions.

31. A device for the cutting of a plastic tube and the sterile sealing of the resulting tube ends comprising a pair of aligned clamp members having clamping jaws for flattening a tube section of a tube inserted into and across said clamp members, a cutting member movable into the space between said clamp members for cutting through the flattened tube section to create a pair of tube ends, a heated wafer for contacting and melting the exposed faces of the tube ends, a pair of exposed quenching depressions into which the heated tube ends may be inserted to lower the temperature of the heated tube ends to seal the tube ends, said wafer including a flat surface perpendicular to the longitudinal axis of said clamp members, and said wafer having a pair of oppositely extending wings perpendicular to said flat surface whereby said flat surface may be disposed against the exposed faces of the tube ends and said wings may penetrate into the lumens of the tube ends.

32. The device of claim 31 wherein said jaws have tube clamping surfaces, and said wings being dimensioned to extend into said clamp members inwardly of said tube clamping surfaces.

33. The device of claim 32 including a slight relief step inwardly of each of said clamp jaws.

34. The device of claim 33 wherein said relief step has a height of about 20 mils.

* * * * *